(12) United States Patent
Ruland et al.

(10) Patent No.: US 7,419,552 B2
(45) Date of Patent: Sep. 2, 2008

(54) C₁₀-ALKANOL ALKOXYLATES AND THE USE THEREOF

(75) Inventors: Alfred Ruland, Schriesheim (DE); Martin Scholtissek, Wachenheim (DE); Guenter Oetter, Frankenthal (DE); Klaus Taeger, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 386 days.

(21) Appl. No.: 10/510,715

(22) PCT Filed: Apr. 25, 2003

(86) PCT No.: PCT/EP03/04334

§ 371 (c)(1), (2), (4) Date: Oct. 18, 2004

(87) PCT Pub. No.: WO03/091191

PCT Pub. Date: Nov. 6, 2003

(65) Prior Publication Data

US 2005/0181967 A1    Aug. 18, 2005

(30) Foreign Application Priority Data

Apr. 26, 2002  (DE)  ................ 102 18 754
Sep. 18, 2002  (DE)  ................ 102 43 360

(51) Int. Cl.
*B08B 3/04* (2006.01)
*C11D 1/722* (2006.01)
*C11D 3/37* (2006.01)

(52) U.S. Cl. ............... 134/39; 134/25.2; 134/25.3; 134/40; 134/41; 134/42; 510/342; 510/360; 510/421; 510/475; 510/505; 8/94.1 R

(58) Field of Classification Search ........ 510/342, 510/360, 421, 475, 505; 134/25.2, 25.3, 134/39, 40, 41, 42; 8/94.1 R
See application file for complete search history.

(56) References Cited

U.S. PATENT DOCUMENTS

| 2,508,036 | A | 5/1950 | Kosmin |
| 2,921,089 | A | 1/1960 | Hagemeyer, Jr. et al. |
| 4,287,370 | A | 9/1981 | Harris et al. |
| 5,340,495 | A | 8/1994 | Mulcahy et al. |
| 5,434,313 | A | 7/1995 | Harrison et al. |
| 5,705,476 | A * | 1/1998 | Hoffarth ............ 510/535 |
| 6,680,412 | B2 * | 1/2004 | Gumbel et al. ......... 568/672 |

FOREIGN PATENT DOCUMENTS

| DE | 42 37 178 | | 5/1994 |
| EP | 0 050 228 | | 4/1982 |
| EP | 0 616 026 | | 9/1994 |
| EP | 0 616 028 | | 9/1994 |
| EP | 0 620 270 | | 10/1994 |
| EP | 0 681 865 | | 11/1995 |
| WO | 94/11330 | | 5/1994 |
| WO | 94/11331 | | 5/1994 |
| WO | WO 94/11331 | * | 5/1994 |
| WO | 95/27034 | | 10/1995 |
| WO | 98/06312 | | 2/1998 |
| WO | 01/04183 | | 1/2001 |
| WO | WO 01/04183 | * | 1/2001 |
| WO | 01/32820 | | 5/2001 |

OTHER PUBLICATIONS

Beilstein E IV 1, p. 3268, no date given.
"Aldehydes, Aliphatic and Araliphatic", Ullmanns Encyclopedia of Industrial Chemistry, 5th ed., vol. A1, pp. 323-328, no date given.
Roempp. Chemie Lexikon, 9th ed., p. 91, no date given.
Marcel Guerbert, C.R. Acad. Sci. Paris 128, 511, pp. 1002-1004.
Veibel, S. et al. "On the Mechanism of the Guerbet Reaction", Tetrahedron, vol. 23, pp. 1723-1733 1967.
Gee, Geoffrey et al. "The Polymerization of Epoxides. Part III. The Polymerization of Propylene Oxide by Sodium Alkoxides", J. Chem. Soc., pp. 4298-4303 1961.
Wojtech, V. B. et al. "Zur Darstellung hochmolekularer Polyaethylenoxyde", Makromol. Chem., vol. 66, pp. 180-195 1966.
Edited by Plesch, P.H. "The Chemistry of Cationic Polymerization", Pergamon Press, New York, pp. 45-94 1963.
Tai, Louis Ho Tan. "Formulating Detergents and Personal Care Products: A Guide to Product Development", AOCS Press, pp. 209-226 2000.

* cited by examiner

*Primary Examiner*—Brian P Mruk
(74) *Attorney, Agent, or Firm*—Oblon, Spivak, McClelland, Maier & Neustadt, P.C.

(57) ABSTRACT

Alkoxylates of the formula (I)

$$C_5H_{11}CH(C_3H_7)CH_2O(A)_n(CH_2CH_2O)_mH \quad (I)$$

where
A is propyleneoxy, buteneoxy or penteneoxy,
n is a number in the range from 1 to 8,
m is a number in the range from 2 to 20,
are used as emulsifier, foam regulator and as wetting agent for hard surfaces.

15 Claims, No Drawings

$C_{10}$-ALKANOL ALKOXYLATES AND THE USE THEREOF

The present invention relates to the use of $C_{10}$-alkanol alkoxylates, to $C_{10}$-alkanol alkoxylates of this type and to processes for their preparation.

Alkoxylates of aliphatic alcohols are used widely as surfactants and emulsifiers. The wetting and emulsifier properties here depend heavily on the type of alcohol and on the type and amount of the alkoxide adducts.

WO 94/11331 relates to the use of alkoxylates of 2-propylheptanol in detergent compositions for degreasing hard surfaces. The alkoxylates have 2 to 16 alkylene oxide groups. The majority of the alkylene oxide groups is preferably in the form of ethylene oxide. According to the examples, exclusively ethoxylated alcohols are used. It is also described that the alcohols can firstly be reacted with ethylene oxide and then with propylene oxide. However, no examples or properties are given for such alkoxylates. It is stated that the described alkoxylates exhibit good detergency and wetting action, combined with low foaming. Additionally, it is stated that the alkoxylates have a desired thickening effect in formulations.

WO 94/11330 relates to alkoxylates of 2-propylheptanol and to the use thereof. The alkoxylates contain 2-propylheptanol reacted firstly with 1 to 6 mol of propylene oxide and then with 1 to 10 mol of ethylene oxide. According to the examples, a 2-propylheptanol reacted firstly with 4 mol of propylene oxide and then with 6 mol of ethylene oxide is used. It is stated that the alkylene oxide adducts exhibit an improved ratio of foaming behavior to detergency. In addition, it is stated that the alkoxylates exhibit a good wetting behavior. They are used in detergent compositions for cleaning textile materials.

U.S. Pat. No. 2,508,036 relates to the use of 2-n-propylheptanol ethoxylates which contain 5 to 15 mol of ethylene oxide as wetting agents in aqueous solutions. It is described that the products can be used as surfactants in detergents. Processes for the alkoxylation of 2-propylheptanol are known in principle from the prior art. For example, WO 01/04183 describes a process for the ethoxylation of hydroxy-functional starter compounds which is carried out in the presence of a double-metal cyanide compound as catalyst.

It is an object of the present invention to provide alkanol alkoxylates which are suitable as emulsifier, foam regulator and as wetting agent for hard surfaces. The alkoxylates should exhibit, in particular, good emulsifying behavior and a low contact angle on hard surfaces upon use. In addition, they should reduce the interfacial tension in liquid systems. The alkoxylates should in general exhibit an advantageous property spectrum when used as emulsifier, foam regulator or as wetting agent. Furthermore, the products should have a favorable ecological profile, i.e. not be aquatoxic: EC 50 values for algae, daphnia or fish greater than 10 mg/l; and also be readily degradable in accordance with OECD 301 A-F. For this, the residual alcohol content should be reduced compared with the ethoxylates. This should prevent the odor, perceived as being undesirable for large numbers of applications, caused by the residual alcohol content.

We have found that this object is achieved according to the invention by the use of alkoxylates of the formula (I)

where
A is buteneoxy, penteneoxy or preferably propylenoxy,
n is a number in the range from 1 to 8,
m is a number in the range from 2 to 20, as emulsifier, foam regulator and as wetting agent for hard surfaces. We have found that the above alkoxylates of the formula (I) exhibit excellent emulsifier properties and can be used as nonfoaming or low-foaming wetting agents for hard surfaces. The alkoxylates exhibit low contact angles in the case of the wetting of hard surfaces and permit the establishment of low interfacial tensions in liquid systems.

The alkoxylates of the formula (I) can thus particularly advantageously be used in surfactant formulations for cleaning hard surfaces, in humectants, cosmetic, pharmaceutical and crop protection formulations, paints, coating compositions, adhesives, leather degreasing compositions, formulations for metalworking, food industry, water treatment, paper industry, fermentation, mineral processing and in emulsion polymerizations. Further details on the individual fields of use are given below.

In the formula (I), n is preferably a number in the range from 1 to 6, particularly preferably from 1 to 4, in particular from 1.3 to 2.3. According to a specifically preferred embodiment, n is a number in the range from 1.2 to 1.8, particularly preferably 1.3 to 1.7, in particular 1.4 to 1.6, specifically about 1.5. m is preferably a number in the range from 3 to 14, particularly preferably 3 to 10.

In the alkoxylates according to the invention, propyleneoxy units are firstly joined to the alcohol radical, followed by ethyleneoxy units. If n and m have a value greater than 1, then the corresponding alkoxy radicals are in block form. n and m refer here to a mean value, which arises as an average for the alkoxylates. n and m may therefore also deviate from whole-number values. In the alkoxylation of alkanols, a distribution of the degree of alkoxylation is generally obtained, which can be adjusted to a certain extent through the use of different alkoxylation catalysts. In the alkoxylates used according to the invention, the alkanol has been reacted firstly with propylene oxide and then with ethylene oxide.

The invention also relates to alkoxylates of the formula (I)

where
A is buteneoxy, penteneoxy or preferably propyleneoxy,
n is a number in the range from greater than 1 to less than 2, in particular 1.2 to 1.8, if
A is buteneoxy, from 1 to 1.8, preferably 1.2 to 1.8,
m is a number in the range from 3 to 14.

Here, n is preferably a number in the range from 1.3 to 1.7, in particular from 1.4 to 1.6. Especially preferably, n has a value of about 1.5. m is preferably a number in the range from 3 to 12, particularly preferably from 3 to 10, specifically 5 to 10.

In the formula (I), the radical $C_5H_{11}$ can have the meaning n-$C_5H_{11}$, $C_2H_5CH(CH_3)CH_2$ or $CH_3CH(CH_3)CH_2CH_2$. It is also possible for mixtures of two or more of these compounds to be present. For example, the alkoxylates may be mixtures where
70 to 99% by weight, preferably 85 to 96% by weight, of alkoxylates A1 are present in which $C_5H_{11}$ has the meaning n-$C_5H_{11}$ hat, and
1 to 30% by weight, preferably 4 to 15% by weight, of alkoxylates A2 in which $C_5H_{11}$ has the meaning $C_2H_5CH(CH_3)CH_2$ and/or $CH_3CH(CH_3)CH_2CH_2$.

The formula (I) thus also covers mixtures of this type. In the formula (I), the radical $C_3H_7$ preferably has the meaning n-$C_3H_7$.

The propylheptanol present in the alkoxylates can be obtained starting from valeraldehyde by aldol condensation and subsequent hydrogenation. The preparation of valeraldehyde and the corresponding isomers takes place by hydroformylation of butene, as described, for example, in U.S. Pat. No. 4,287,370; Beilstein E IV 1, 32 68, Ullmanns Encyclopedia of Industrial Chemistry, 5th Edition, Volume A1, pages 323 and 328 f. The subsequent aldol condensation is described, for example, in U.S. Pat. No. 5,434,313 and Römpp, Chemie Lexikon, 9th Edition, keyword "Aldol-Addition" page 91. The hydrogenation of the aldol condensation product follows general hydrogenation conditions.

Furthermore, 2-propylheptanol can be prepared by condensation of 1-pentanol (as a mixture of the corresponding 1-methylbutanols) in the presence of KOH at elevated temperatures, see e.g. Marcel Guerbet, C. R. Acad Sci Paris 128, 511, 1002 (1899). Furthermore, reference is made to Römpp, Chemie Lexikon, 9th Edition, Georg Thieme Verlag Stuttgart, and the citations given therein, and also to Tetrahedron, Vol. 23, pages 1723 to 1733.

The alkoxylates of the formula (1) can be obtained according to the invention by reacting alcohols of the formula $C_5H_{11}CH(C_3H_7)CH_2OH$ firstly with propylene oxide and then with ethylene oxide under alkoxylation conditions. Suitable alkoxylation conditions are described, for example, in Nikolaus Schönfeldt, Grenzflächenaktive Äthylenoxid-Addukte [Interface-active ethylene oxide adducts], Wissenschaftliche Verlagsgesellschaft mbH Stuttgart, 1984. The alkoxylation can be carried out, for example, using alkaline catalysts, such as alkali metal hydroxides, alkali metal alkoxides. The use of these catalysts results in specific properties, in particular the distribution of the degree of alkoxylation.

The alkoxylation can additionally be carried out using Lewis-acidic catalysis with the specific properties resulting therefrom, in particular in the presence of $BF_3 \times H_3PO_4$, $BF_3$ dietherate, $SbCl_5$, $SnCl_4 \times 2H_2O$, hydrotalcite. Double-metal cyanide (DMC) compounds are also suitable as catalysts.

In this process, the excess alcohol can be distilled off, or the alkoxylate can be obtained by a two-stage process. The preparation of mixed alkoxylates from, for example, EO and PO is also possible, in which case firstly a polyethylene oxide block can join to the alkanol radical, and then an ethylene oxide block, or firstly an ethylene oxide block and then a propylene oxide block. Preferred reaction conditions are given below.

The alkoxylation is preferably catalyzed by strong bases, which are expediently added in the form of an alkali metal hydroxide or alkaline earth metal hydroxide, usually in an amount of from 0.1 to 1% by weight, based on the amount of alkanol (cf. G. Gee et al., J. Chem. Soc. (1961), p. 1345; B. Wojtech, Makromol. Chem. 66, (1966), p. 180).

An acidic catalysis of the addition reaction is also possible. In addition to Bronsted acids, Lewis acids are also suitable, such as, for example, $AlCl_3$ or $BF_3$ dietherate, $BF_3 \times H_3PO_4$, $SbCl_4 \times 2H_2O$, hydrotalcite (cf. P. H. Plesch, The Chemistry of Cationic Polymerization, Pergamon Press, New York (1963). Double-metal cyanide (DMC) compounds are also suitable as catalyst.

In principle, the DMC compounds which can be used are all suitable compounds known to the person skilled in the art.

DMC compounds suitable as catalyst are described, for example, in WO 99/16775 and DE 10117273.7. In particular, double-metal cyanide compounds of the formula I are suitable as catalyst for the alkoxylation:

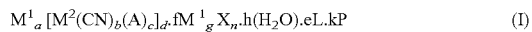

$$M^1_a[M^2(CN)_b(A)_c]_d \cdot fM^1_g X_n \cdot h(H_2O) \cdot eL \cdot kP \qquad (I)$$

in which $M^1$ is at least one metal ion chosen from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, $Ru^{3+}$, $M^2$ is at least one metal ion chosen from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$, A and X, independently of one another, are an anion chosen from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or hydrogencarbonate, L is a water-miscible ligand chosen from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphites, phosphanes, phosphonates and phosphates, k is a fraction or integer greater than or equal to zero, and P is an organic additive, a, b, c, d, g and n are chosen so that the electroneutrality of the compound (I) is ensured, where c may be 0, e is the number of ligand molecules and is a fraction or integer greater than 0 or 0, f, h and m, independently of one another, are a fraction or integer greater than 0 or 0.

Organic additives P to be mentioned are: polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose, polyacetates, ionic surface-active and interface-active compounds, bile acid or its salts, esters or amides, carboxylic esters of polyhydric alcohols and glycosides.

These catalysts may be crystalline or amorphous. For the case where k is zero, crystalline double-metal cyanide compounds are preferred. In the case where k is greater than zero, either crystalline, partially crystalline or substantially amorphous catalysts are preferred.

There are various preferred embodiments of the modified catalysts. A preferred embodiment is catalysts of the formula (I) in which k is greater than zero. The preferred catalyst then comprises at least one double-metal cyanide compound, at least one organic ligand and at least one organic additive P.

In another preferred embodiment, k is zero, optionally e is also zero and X is exclusively a carboxylate, preferably formate, acetate and propionate. Such catalysts are described in WO 99/16775. In this embodiment, crystalline double-metal cyanide catalysts are preferred. Also preferred are double-metal cyanide catalysts as described in WO 00/74845 which are crystalline and flake-like.

The modified catalysts are prepared by combining a metal salt solution with a cyanometallate solution, which may optionally comprise both an organic ligand L and also an organic additive P.

Then, the organic ligand and optionally the organic additive are added. In a preferred embodiment of the catalyst preparation, an inactive double-metal cyanide phase is firstly prepared and this is then converted into an active double-metal cyanide phase by recrystallization, as described in PCT/EP01/01893.

In another preferred embodiment of the catalysts, f, e and k are not equal to zero. These are double-metal cyanide catalysts which contain a water-miscible organic ligand (generally in amounts of from 0.5 to 30% by weight) and an organic additive (generally in amounts of from 5 to 80% by weight), as described in WO 98/06312. The catalysts can either be prepared with vigorous stirring (24 000 rpm using Turrax) or with stirring, as described in U.S. Pat. No. 5,158,922.

Particularly suitable as catalyst for the alkoxylation are double-metal cyanide compounds which comprise zinc, cobalt or iron or two thereof. Berlin Blue, for example, is particularly suitable.

Preference is given to using crystalline DMC compounds. In a preferred embodiment, a crystalline DMC compound of the Zn-Co type is used as catalyst which comprises zinc acetate as further metal salt component. Such compounds crystallize in monoclinic structure and have a flake-like habit. Such compounds are described, for example, in WO 00/74845 or PCT/EP01/01893.

DMC compounds suitable as catalysts can, in principle, be prepared by all methods known to the person skilled in the art. For example, the DMC compounds can be prepared by direct precipitation, "incipient wetness" method, by the preparation of a precursor phase and subsequent recrystallization.

The DMC compounds can be used as powder, paste or suspension or be shaped to give a shaped body, be transformed into shaped bodies, foams or the like or be deposited on shaped bodies, foams or the like.

The catalyst concentration used for the alkoxylation is, based on the final quantity structure, typically less than 2 000 ppm, preferably less than 1 000 ppm, in particular less than 500 ppm, particularly preferably less than 100 ppm, for example less than 50 ppm or 35 ppm, especially preferably less than 25 ppm.

The addition reaction is carried at temperatures of from about 90 to about 240° C., preferably from 120 to 180° C., in a closed vessel. The alkylene oxide or the mixture of different alkylene oxides is added to the mixture of alkanol (mixture) according to the invention and alkali under the vapor pressure of the alkylene oxide mixture which prevails at the chosen reaction temperature. If desired, the alkylene oxide can be diluted by up to about 30 to 60% with an inert gas. This ensures additional safety against explosion-like polyaddition of the alkylene oxide.

If an alkylene oxide mixture is used, then polyether chains are formed in which the various alkylene oxide building blocks are distributed in a virtually random manner. Variations in the distribution of the building blocks along the polyether chain arise on the basis of different reaction rates of the components and can also be achieved voluntarily through the continuous introduction of an alkylene oxide mixture of program-controlled composition. If the different alkylene oxides are reacted one after the other, polyether chains are obtained which have a block-like distribution of the alkylene oxide building blocks.

The length of the polyether chains varies within the reaction product statistically about an average value which essentially corresponds to the stoichiometric value which arises from the amount added.

The alkoxylation is generally carried out in the presence of basic catalysts such as KOH without a diluent. However, the alkoxylation can also be carried out with the co-use of a solvent. To prepare the alkoxylates according to the invention, the alcohols are firstly reacted with a suitable amount of propylene oxide and then with a suitable amount of ethylene oxide. In the process, a polymerization of the alkylene oxide is set in motion in which a random distribution of homologues inevitably results, the average value of which is given in the present case by n and m.

As a result of the propoxylation carried out first according to the invention and ethoxylation which is only carried out subsequently, it is possible to reduce the content of residual alcohol in the alkoxylates since propylene oxide is added more uniformly to the alcohol component. In contrast thereto, ethylene oxide preferably reacts with ethoxylates, meaning that in the case of an initial use of ethylene oxide for the reaction with the alkanols, both a broad homologue distribution and also a high content of residual alcohol result. The avoidance of relatively large amounts of residual alcohol present in the product is particularly advantageous for odor reasons. The alcohols used according to the invention generally have an intrinsic odor which can be largely suppressed by complete alkoxylation. Alkoxylates obtained by customary processes have a high intrinsic odor which is undesired for many applications.

According to the invention, it is not necessary and not desired for a large residual content of alcohol to the present in the alkoxylates according to the invention. According to one embodiment of the invention, the alkoxylates and mixtures thereof are largely free from alcohols.

The alkoxylates according to the invention exhibit improved wetting on hard surfaces, in particular compared with corresponding alcohols which have only been ethoxylated or have been firstly ethoxylated and then propoxylated. Products which have firstly been ethoxylated and then propoxylated exhibit a wetting behavior which is largely identical to that of products which have only been ethoxylated, but the advantageous wetting properties according to the invention are not obtained.

The advantageous wetting behavior of the compounds according to the invention can, for example, be determined by measuring the contact angle on glass, polyethylene oxide or steel. The improved wetting behavior leads to better performance in the case, in particular, of cleaning processes. This is surprising since the chain lengthening of the starting alcohol usually diminishes the dynamic and wetting properties. The alkoxylates according to the invention can thus be used to increase the wetting rate of aqueous formulations. The alkoxylates according to the invention can thus also be used as solubilizers which, in particular, do not have a negative effect on the wetting ability of wetting auxiliaries even in dilute systems, but have a positive effect. They can be used for increasing the solubility of wetting auxiliaries in aqueous formulations which comprise nonionic surfactants. In particular, they are used for increasing the wetting rate in aqueous wetting agents.

In addition, the alkoxylates according to the invention are used for reducing interfacial tension, for example in aqueous surfactant formulations. The reduced interfacial tension can be determined, for example, by the pendant drop method. From this also arises a better action of the alkoxylates according to the invention as emulsifier or coemulsifier. The alkoxylates according to the invention can also be used for reducing the interfacial tension in short times of, customarily, less than one second or for accelerating the establishment of the interfacial tension in aqueous surfactant formulations.

The present invention likewise provides cleaning, wetting, coating, adhesive, leather fat-liquoring, humectant or textile-treatment compositions or cosmetic, pharmaceutical or crop protection formulations which comprise at least one alkoxylate of the formula (I) as defined above. The compositions preferably comprise 0.1 to 20% by weight of the alkoxylates.

Preferred fields of use for the alkoxylates according to the invention are described in more detail below.

The alkoxylates according to the invention are preferably used in the following areas:

- surfactant formulations for cleaning hard surfaces: suitable surfactant formulations to which the alkoxylates according to the invention can be added are described, for example, in Formulating Detergents and Personal Care Products by Louis Ho Tan Tai, AOCS Press, 2000. They comprise, for example as further components, soaps, anionic surfactants such as LAS or paraffin sulfonates or FAS or FAES, acid, such as phosphoric acid, amidosulfonic acid, citric acid, lactic acid, acetic acid, other organic and inorganic acids, solvents, such as ethylene glycol, isopropanol, complexing agents, such as EDTA, NTA, MGDA, phosphonates, polymers, such as polyacrylates, maleic acid-acrylic acid copolymers, alkali donors, such as hydroxides, silicates, carbonates, perfume oils, oxidizing agents, such as perborates, peracids or trichloroisocyanuric acid, Na or K dichloroisocyanurates, enzymes; see also Milton J. Rosen, Manilal Dahanayake, Industrial Utilization of Surfactants, AOCS Press, 2000 and Nikolaus Schönfeldt, Grenzflächenaktive Ethylenoxidaddukte [Interface-active ethylene oxide adducts]. These also in principle cover formulations for the other said applications. These may be household cleaners, such as all-purpose cleaners, dishwashing detergents for manual and automatic dishwashing, metal degreasing, industrial applications such as cleaners for the food industry, bottle washing, etc. They may also be printing roll and printing plate cleaning compositions in the printing industry. Suitable further ingredients are known to the person skilled in the art.
- Humectants, in particular for the printing industry.
- Cosmetic, pharmaceutical and crop protection formulations. Suitable crop protection formulations are described, for example, in EP-A-0 050 228. Further ingredients customary for crop protection compositions may also be present.
- Paints, coating compositions, inks, pigment preparations and adhesives in the coating and polymer film industry.
- Leather degreasing compositions.
- Formulations for the textile industry, such as leveling agents or formulations for yarn cleaning.
- Fiber processing and auxiliaries for the paper and pulp industry.
- Metal processing, such as metal refining and electroplating sector.
- Food industry.
- Water treatment and drinking water production.
- Fermentation.
- Mineral processing and dust control.
- Building auxiliaries.
- Emulsion polymerization and preparation of dispersions.
- Coolants and lubricants.

Such formulations usually comprise ingredients such as surfactants, builders, fragrances and dyes, complexing agents, polymers and other ingredients. Typical formulations are described, for example, in WO 01/32820. Further ingredients suitable for different applications are described in EP-A-0 620 270, WO 95/27034, EP-A-0 681 865, EP-A-0 616 026, EP-A-0 616 028, DE-A-42 37 178 and U.S. Pat. No. 5,340,495 by way of example.

In general, the alkoxylates according to the invention can be used in all fields where the action of interface-active substances is necessary.

The structures according to the invention have better environmental and skin compatibility than known structures, meaning that they are advantageously suitable for a large number of fields of application.

The invention is described in more detail by the examples below.

EXAMPLES

Preparation of the Alkoxylates

Example 1

2-Propylheptanol+1.5 PO+6 EO 790 g of 2-propylheptanol were introduced together with 8.5 g of KOH, 45% in water, into an autoclave and dewatered at 80° C. and under reduced pressure (about 20 mbar). Then at 120 to 130° C., 518 ml of propylene oxide were added and left to fully react at this temperature under increased pressure. The end of the reaction could be observed from a change in the pressure. 1470 ml of ethylene oxide were then metered in at 145 to 155° C. over a prolonged period at increased pressure and likewise left to fully react. After flushing with inert gas and cooling to room temperature, the catalyst was neutralized by adding 3.8 ml of glacial acetic acid.

Example 2

2-Propylheptanol+1.5 PO+8 EO

Reaction as in Example 1, the alkoxylation of 2-propylheptanol was carried out following the addition of 45% strength KOH and subsequent dewatering at about 80° C. with propylene oxide and then with ethylene oxide in the corresponding stoichiometric ratios under conditions as given in Example 1. The neutralization was carried out analogously to Example 1.

Example 3

2-Propylheptanol+1.5 PO+10 EO 630 g of 2-propylheptanol were introduced together with 9.1 g of KOH, 45% in water, into an autoclave and dewatered at 80° C. and under reduced pressure (about 20 mbar). Then at 120 to 130° C., 414 ml of propylene oxide were added and left to fully react at this temperature under increased pressure. The end of the reaction could be observed from a change in the pressure. 1990 ml of ethylene oxide were then metered in at 145 to 155° C. over a prolonged period at increased pressure and likewise left to fully react. After flushing with inert gas and cooling to room temperature, the catalyst was neutralized by adding 4.0 ml of glacial acetic acid.

Comparative Example C1

2-Propylheptanol+8 EO

Reaction as in Example 1; the reaction with PO at a lower temperature was omitted and 2-propylheptanol was reacted directly at 145-155° C. with 8 mol of EO; the neutralization was carried out analogously to Example 1.

Comparative Example C2

2-Propylheptanol+8 EO+1.5 PO

Reaction as in Example 1; except that 2-propylheptanol was reacted firstly with 8 mol of EO at 145-155° C. and then reacted with 1.5 mol of PO at 120-130° C.; the neutralization was carried out analogously to Example 1.

APPLICATION EXAMPLES

The alkoxylates according to the invention and the comparison alkoxylates were used for wetting glass, polyethylene and steel. Here, the contact angle for a concentration of 0.2 g/l in water was measured at a temperature of 40° C. The results are summarized in the tables below.

Interfacial Tension

The interfacial tension was measured at a concentration of 1 µl at 25° C. in hexadecane and olive oil. The measurement was carried out in accordance with the pendant drop method. The results are likewise given in the tables below.

Contact angle on V2A-grade steel, [degrees]

| Time (sec) | 2-PH + 1.5 PO + 8 EO | 2-PH + 8 EO + 1.5 PO | 2-PH + 8 EO | Demin. Water |
|---|---|---|---|---|
| 0.1 sec | 48 | 46 | 48 | 65 |
| 1 sec | 43 | 45 | 48 | 65 |
| 10 sec | 32 | 40 | 46 | 64 |

Contact angle on polyethylene [degrees]

| Time (sec) | 2-PH + 1.5 PO + 8 EO | 2-PH + 8 EO + 1.5 PO | 2-PH + 8 EO | Demin. Water |
|---|---|---|---|---|
| 0.1 sec | 57 | 58 | 65 | 96 |
| 1 sec | 52 | 57 | 64 | 96 |
| 10 sec | 40 | 54 | 64 | 95 |

Contact angle on glass [degrees]

| Time (sec) | 2-PH + 1.5 PO + 8 EO | 2-PH + 8 EO + 1.5 PO | 2-PH + 8 EO | Demin. Water |
|---|---|---|---|---|
| 0.1 sec | 37 | 39 | 38 | 41 |
| 1 sec | 32 | 33 | 32 | 40 |
| 10 sec | 20 | 24 | 25 | 39 |

Wetting on cotton, EN 1/72, 23, 0.1 g/l, 2 g/l of soda in dist. water

| | 2-PH + 1.5 PO + 8 EO | 2-PH + 8 EO + 1.5 PO | 2-PH + 8 EO |
|---|---|---|---|
| Time (sec) | 10 | 17 | 15 |

Residual alcohol 2-PH, determined by gas chromatography using an internal standard

| | 2-PH + 1.5 PO + 8 EO | 2-PH + 8 EO + 1.5 PO | 2-PH + 8 EO |
|---|---|---|---|
| g/100 g | 0.8 | 1.9 | 4.3 |

Interfacial tension, pendant drop method, 1 g/l, 25° C., values after 10 min.

| (mN/m) | 2-PH + 1.5 PO + 8 EO | 2-PH + 8 EO + 1.5 PO | 2-PH + 8 EO |
|---|---|---|---|
| Hexadecane | 7.7 | 13.9 | 13.2 |
| Olive oil | 5.2 | 8.0 | 8.4 |

2nd Example

Contact angle on V2A-grade steel, [degrees]

| Time (sec) | 2-PH + 1.5 PO + 6 EO | 2-PH + 6 EO + 1.5 PO | 2-PH + 6 EO | Demin. Water |
|---|---|---|---|---|
| 0.1 sec | 42 | 46 | 48 | 65 |
| 1 sec | 35 | 43 | 46 | 65 |
| 10 sec | 23 | 37 | 42 | 64 |

Contact angle on polyethylene [degrees]

| Time (sec) | 2-PH + 1.5 PO + 6 EO | 2-PH + 6 EO + 1.5 PO | 2-PH + 6 EO | Demin. Water |
|---|---|---|---|---|
| 0.1 sec | 55 | 56 | 62 | 96 |
| 1 sec | 48 | 54 | 61 | 96 |
| 10 sec | 36 | 48 | 59 | 95 |

Contact angle on glass [degrees]

| Time (sec) | 2-PH + 1.5 PO + 6 EO | 2-PH + 6 EO + 1.5 PO | 2-PH + 6 EO | Demin. Water |
|---|---|---|---|---|
| 0.1 sec | 28 | 32 | 36 | 42 |
| 1 sec | 21 | 24 | 31 | 41 |
| 10 sec | 9 | 17 | 22 | 40 |

Wetting on cotton, EN 1772, 23° C., 1 g/l, 2 g/l of soda in dist. water

| | 2-PH + 1.5 PO + 6 EO | 2-PH + 6 EO + 1.5 PO | 2-PH + 6 EO |
|---|---|---|---|
| g/100 g | 1.4 | 13 | 10 |

| | Residual alcohol 2-PH, determined by gas chromatography using an internal standard | | |
|---|---|---|---|
| | 2-PH + 1.5 PO + 6 EO | 2-PH + 6 EO + 1.5 PO | 2-PH + 6 EO |
| g/100 g | 1.4 | 2.7 | 7.8 |

| | Interfacial tension, pendant drop method, 1 g/l, 25° C., values after 10 min. | | |
|---|---|---|---|
| (mN/m) | 2-PH + 1.5 PO + 6 EO | 2-PH + 6 EO + 1.5 PO | 2-PH + 6 EO |
| Hexadecane | 8.3 | 11.1 | 13.1 |
| Olive oil | 6.7 | 7.5 | 9.0 |

The smaller the contact angle and the shorter the time in which it is established, the better the wetting. The lower the interfacial tension, the greater the interfacial activity and the emulsifiability.

We claim:

1. A composition comprising an alkoxylate of the formula (I)

$$C_5H_{11}CH(C_3H_7)CH_2O(A)_n(CH_2CH_2O)_mH \quad (I)$$

wherein

A is buteneoxy, n is a number in the range from 1 to 1.8, m is a number in the range from 3 to 14, and one or more additives, wherein buteneoxy units are firstly joined the alcohol radical, followed by ethyleneoxy units, wherein the composition is selected from surfactant compositions for the cleaning of hard surface, humectant compositions, cosmetic compositions, adhesive compositions, leather degreasing compositions, compositions for metalworking, compositions for food industry, compositions for water treatment, compositions for paper industry, fermentation compositions, mineral processing compositions and emulsions for polymerizations.

2. The composition as claimed in claim 1, wherein, in the formula (I), the radical $C_5H_{11}$, has the meaning n-$C_5H_{11}$, $C_2H_5CH(CH_3)CH_2$ or $CH_3CH(CH_3)CH_2$, $CH_2$ or mixtures of two or more of these compounds.

3. An alkoxylate of the formula (I)

$$C_5H_{11}CH(C_3H_7)CH_2O(A)_n(CH_2CH_2O)_mH \quad (I)$$

wherein

A is propyleneoxy, buteneoxy or penteneoxy, n is a number in the range from 1 to 1.8, m is a number in the range from 3 to 14, wherein buteneoxy units are firstly joined the alcohol radical, followed by ethyleneoxy units.

4. The alkoxylate as claimed in claim 3, wherein, in the formula (I), n is a number in the range from 1.3 to 1.7 and m is a number in the range from 3 to 12.

5. The alkoxylate as claimed in claims 3, wherein, in the formula (I), the radical $C_5H_{11}$ has the meaning n-$C_5H_{11}$, $C_2H_5CH(CH_3)CH_2$ or $CH_3CH(CH_3)CH_2CH_2$, or mixtures of two or more of these compounds.

6. A process for the preparation of the alkoxylate as claimed in claim 3, comprising reacting an alcohol of the formula $C_5H_{11}CH(C_3H_7)CH_2OH$ first with butylene oxide and then with ethylene oxide under alkoxylation conditions, wherein the alkoxylation is carried out in the presence of a double-metal cyanide compound as catalyst.

7. The process as claimed in claim 6, wherein the alcohol of the formula $C_5H_{11}CH(C_3H_7)CH_2OH$ is obtained by alkaline dimerization of valeraldehyde to give an α,β-unsaturated aldehyde, and subsequent hydrogenation.

8. A method of cleaning a hard surface, comprising contacting the composition of claim 1 with the hard surface.

9. A method of degreasing leather, comprising contacting the composition of claim 1 with leather.

10. A method of processing metal, comprising contacting the composition of claim 1 with metal.

11. A method of treating water, comprising contacting the composition of claim 1 with a supply of water.

12. A method of processing paper, comprising contacting the composition of claim 1 with a paper or pulp source.

13. A method of processing minerals, comprising contacting the composition of claim 1 with a mineral source.

14. A method of polymerization, comprising contacting the composition of claim 1 with one or more monomers.

15. A method of wetting a surface, comprising contacting the composition of claim 1 with the surface.

* * * * *